United States Patent [19]
Haber et al.

[11] Patent Number: 4,834,717
[45] Date of Patent: May 30, 1989

[54] DISPOSABLE, PRE-STERILIZABLE SYRINGE FOR A PRE-FILLED MEDICATION CARTRIDGE

[75] Inventors: Terry M. Haber, Lake Forest; William H. Smedley, Lake Elsinore; Clark B. Foster, El Toro, all of Calif.

[73] Assignee: Habley Medical Technology Corporation, Laguna Hills, Calif.

[21] Appl. No.: 101,251

[22] Filed: Sep. 25, 1987

[51] Int. Cl.$^4$ ............................................... A61M 5/32
[52] U.S. Cl. .................................... 604/193; 604/232
[58] Field of Search ............... 604/192, 193, 196, 198, 604/263, 232

[56] References Cited

U.S. PATENT DOCUMENTS

| | | | |
|---|---|---|---|
| 2,707,466 | 5/1955 | Hoskins et al. | 604/193 |
| 2,880,723 | 4/1959 | Adams | 604/193 |
| 2,888,924 | 6/1959 | Dunmire | 604/196 |
| 3,820,652 | 6/1974 | Thackston | 604/193 X |
| 4,681,567 | 7/1987 | Masters et al. | 604/198 |

Primary Examiner—John D. Yasko
Attorney, Agent, or Firm—Morland C. Fischer

[57] ABSTRACT

A disposable, sterilizable syringe for injecting a fluid medication from a pre-filled cartridge or ampule to a targeted tissue area. The syringe includes an elongated, detachable sheath which performs the functions of both a protective sheathing for surrounding a needle cannula at the distal end of the syringe cylinder and the stem of a piston assembly at the proximal end of the cylinder for expulsing medication from the cartridge. An axially extending guide slot having distally and proximally oriented locking detents is formed through a side of the syringe cylinder. A needle position control button is adapted to ride through the guide slot to cause a needle carrying hub, to which the control button is integrally connected and from which the needle cannula projects, to correspondingly move through the cylinder. Accordingly, the needle position button can be located at the distally oriented locking detent for simultaneously causing the needle cannula to project outwardly and distally from the syringe cylinder, so that an injection can be administered. Or, after the medication cartridge has been emptied, the needle position control button can be selectively relocated through the guide slot to the proximally oriented locking detent, so that the needle cannula can be retracted and locked within the cylinder to permit a safe handling and disposal of the syringe after use.

16 Claims, 3 Drawing Sheets

DISPOSABLE, PRE-STERILIZABLE SYRINGE FOR A PRE-FILLED MEDICATION CARTRIDGE

BACKGROUND OF THE INVENTION

1. Field of the Invention

This invention relates to a relatively low cost, disposable and sterilizable syringe which is adapted to reduce the frequency of accidental and, in some cases, life threatening needle strikes by enabling selective position control of the needle cannula from a position projecting outwardly and distally from the syringe cylinder at which to administer an injection to a retracted and locked position within the cylinder at which the syringe may be safely handled and discarded after use.

2. Prior Art

Hypodermic syringes are used for a variety of injection procedures including the delivery of medicinal drugs and anesthetics to a recipient. However, once the injection procedure is completed and the syringe cylinder emptied, problems may arise as a consequence of failing to properly and adequately dispose of the syringe. By way of an example, the syringe may be used to treat a patient having a communicable disease. To prevent reuse, the hypodermic needle is sometimes broken before the syringe is discarded. Health care workers are susceptible to accidental and potentially infectious needle strikes due to the careless handling of the hypodermic needle from breaking the needle or disposing of the syringe after use. The resulting mini-accidents caused by the inadvertent needle strikes typically require a blood test for such diseases as AIDS and hepatitis. The corresponding cost and inefficiency of testing health care workers who have received an inadvertent needle strike results in considerable waste, which may be particularly damaging to a health care facility striving for economy and efficiency.

The following U.S. patents provide examples of syringes having a hypodermic needle which may be withdrawn into the syringe cylinder after use:

U.S. Pat. No. 2,722,215, Nov. 1, 1955
U.S. Pat. No. 4,026,287, May 31, 1977
U.S. Pat. No. 4,507,117, Mar. 26, 1985
U.S. Pat. No. 4,643,199, Feb. 17, 1987
U.S. Pat. No. 4,650,468, Mar. 17, 1987

One significant problem with some of the syringes listed above lies in the fact that said syringes have no means by which a used hypodermic needle may be safely locked within and permanently shielded by the syringe cylinder, so that the syringe and needle are not easily reuseable. That is to say, little is available in the aforementioned syringes to prevent the needle from being completely removed from the syringe cylinder and/or from being returned to an outwardly projecting position from the cylinder by which to execute another injection procedure. Consequently, the syringe and/or needle may be reused. A greater opportunity exists to handle a used needle which has been removed from or returned to the cylinder, so as to disadvantageously contribute to an accidental needle strike and to the possible spread of disease.

SUMMARY OF THE INVENTION

In general terms, a disposable, sterilizable syringe is disclosed of the type having a medication cartridge or ampule that is pre-filled with a fluid (e.g. an anesthesia) and a double ended hypodermic needle, one end of which communicates with the cartridge at the interior of the syringe cylinder. The syringe is advantageously adapted to decrease the frequency of accidental needle strikes and, thereby, reduce the spread of possibly contagious diseases among health care workers who handle and/or dispose of syringes. The syringe is also characterized by a minimum number of parts and a reduced cost of manufacture.

More particularly, the syringe includes an elongated hollow sheath that performs the functions of both a sheathing by which to protect a needle cannula and a piston stem by which to expulse fluid medication from the cartridge. The hollow sheath may be detachably connected to the distal bore of the syringe cylinder to surround and protect the needle cannula which projects outwardly and distally therefrom. The sheath may be detached from the cylinder bore to expose the needle for administering an injection. The sheath may then be connected at the proximal end of the cylinder to the rubber plunger which is located at one end of the medication cartridge. Hence, the sheath forms a piston stem for driving the rubber plunger through the cartridge and thereby injecting fluid to a targeted tissue area via the needle.

An axially extending guide slot having distally and proximally oriented locking detents is formed through a side of the syringe cylinder. A needle position control button is adapted to ride through the guide slot. The needle position control button is integrally connected to a needle carrying hub which supports and retains the needle at the interior of the cylinder, such that a movement of the needle position control button along the guide slot causes a corresponding relocation of the needle relative to the interior of the cylinder. Accordingly, the needle position control button can be located at the distally oriented locking detent, whereby the needle cannula projects outwardly and distally from the cylinder for administering an injection. After the medication cartridge has been emptied, the needle position control button can be moved through the axial guide slot to the proximally oriented locking detent, whereby the needle cannula is retracted, shielded and locked within the cylinder to permit a safe handling and disposal of the syringe after use.

DESCRIPTION OF THE PREFERRED EMBODIMENT

Figure 1:
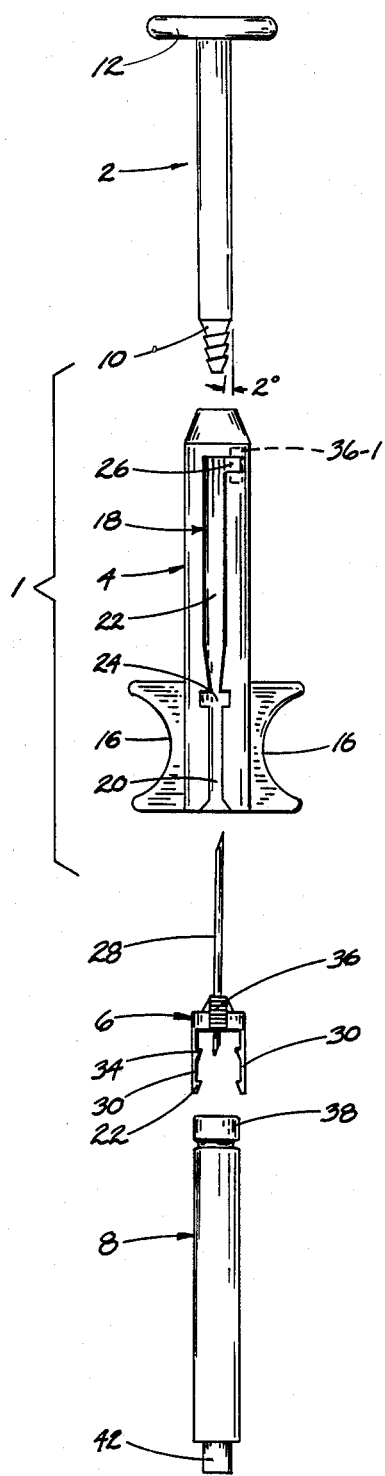
FIG. 1 is an exploded view of the disposable, sterilizable syringe which forms the present invention.
Figure 2:
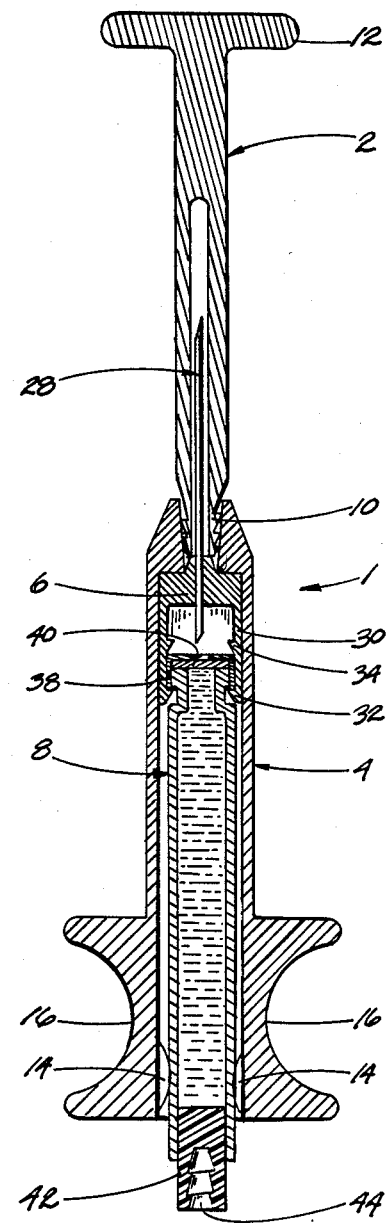
FIG. 2 is a cross-section of the syringe of FIG. 1 in an assembled condition suitable for packaging and sterilization.

The disposable syringe which forms the present invention is best described while referring to the drawings, where, in FIG. 1, there is shown an exploded view of syringe 1, and, in FIG. 2, there is shown the assembled syringe suitable for packaging and sterilization. Referring concurrently to FIGS. 1 and 2, the syringe 1 includes a needle sheath 2, a syringe cylinder 4, a needle carrying hub 6, and a fluid medication cartridge or ampule 8. The needle sheath 2 is an elongated member having a generally hollow body that is preferably fabricated from plastic and performs the functions of both a protective sheathing to surround a needle cannula (best illustrated in FIG. 2) and a piston stem to expulse fluid from the cartridge 8 (best shown in FIGS. 4 and 5). A thread 10 is formed at a first end of needle sheath 2 to be received within the distal bore of syringe cylinder 4. The thread 10 is provided with a slight (e.g. 2°) taper to enable needle sheath 2 to be press fit within and releasably retained by the distal bore of cylinder 4 while syringe 1 is in the packaged configuration of FIG. 2. The opposite end of needle sheath 2 includes a position control flange 12 by which the movement of the needle sheath 2 through the syringe cylinder 4 is controlled when the sheath is used as a piston stem, in a manner that will be described in greater detail hereinafter.

The syringe cylinder 4 has a generally hollow body which is formed from a resilient (i.e. spring-like) material and is suitably sized to receive the cartridge 8 therewithin. A series of (e.g. three) guide bumps 14 extend radially inward from evenly spaced locations around the proximal end of cylinder 4. The guide bumps 14 function to guide and stabilize (i.e. prevent wiggle of) the cartridge 8 when such cartridge is moved through the hollow interior of cylinder 4. A pair of finger ledges 16 extend radially outward from the proximal end of cylinder 4 at opposite sides thereof. An axial guide slot 18 extends through one side of the syringe cylinder 4 (best shown in FIG. 1) between the proximal and distal ends thereof. The guide slot 18 comprises the interconnection of a relatively narrow, proximally oriented guide portion 20, a relatively wide, distally oriented guide portion 22, and a needle retraction detent 24 location therebetween. The guide slot 18 is tapered at the intersection of the distally oriented guide portion 22 with needle retraction detent 24. Coextensively formed with and projecting perpendicularly from the distally oriented guide portion 22 of guide slot 18 is a needle extension detent 26, which, as is best illustrated in FIG. 1, is disposed adjacent the distal bore of cylinder 4.

The needle carrying hub 6 is molded to a coaxially aligned, double ended hypodermic needle 28, such that one end of needle 28 projects distally from the hub for injecting a fluid, while the opposite end of needle 28 projects proximally from the hub for communicating with the interior of syringe cylinder 4 (and with the fluid contents of cartridge 8). Needle carrying hub 6 includes a plurality of (e.g. three) proximally projecting flexible arms 30 by which to receive and retain the medication cartridge 8. That is to say, two sets of catches 32 and 34 project radially inward from the arms 30 of hub 6. The sets of catches 32 and 34 are spaced linearly from one another along respective arms 30 so as to selectively control the receipt and position of the cartridge 8 relative to the proximally projecting end of needle 28. Projecting radially outward from the needle hub 6 is an integral needle position control button 36. As will soon be explained, the position control button 36 is adapted to be moved manually through the axial slot 18 of syringe cylinder 4 for the important purpose of controlling the position of the needle 28 relative to cylinder 4.

The medication cartridge or ampule 8 is typically formed from glass and is pre-filled with a fluid medication (e.g. anesthesia), such as Epinephrine, Lidocaine, or the like. A metal sealing cap 38, which surrounds and retains a rubber diaphragm 40 (best shown in FIG. 2), is located at one end of the cartridge 8. A rubber piston 42 is press-fit and retained by friction within the opposite end of cartridge 8. Piston 42 includes a hollow, molded receptacle 44 (also best shown in FIG. 2), the purpose and advantage of which will be disclosed when referring to FIG. 4.

An assembly of the disposable syringe 1 of the present invention into the packaged configuration is now explained in detail while referring particularly to FIG. 2. Initially, the needle carrying hub 6 is loaded through the proximal end of and moved distally through the interior of the syringe cylinder 4, such that the needle position control button 36 rides through the proximal and distal guide portions 20 and 22 of axial slot 18 (of FIG. 1). A suitable tool (not shown) may be used to momentarily separate the walls of the resilient syringe cylinder 4 to facilitate the distal travel of the control button 36 through the axial slot 18 during syringe assembly. In this manner, the hub 6 is located adjacent the distal bore of cylinder 4, so that one end of the needle 28 projects outwardly and distally therefrom. The control button 36 of needle carrying hub 6 is then moved (i.e. rotated) laterally into the needle extension detent 26 of axial slot 18 (illustrated in phantom in FIG. 1 and represented by reference numeral 36-1), whereby to lock the hub 6 adjacent the cylinder bore and thereby prevent the proximal retraction of the needle 28 from the distally projecting position, as shown.

Next, the hollow needle sheath is positioned around the distally projecting end of needle 28 in order to avoid an accidental needle strike and preserve the sterility of the needle. That is, the threaded end 10 of needle sheath 2 is press-fit and detachably retained by friction within the distal bore of cylinder 4, whereby needle 28 is surrounded and protected by the sheath. The assembled configuration is completed when the medication cartridge 8 is loaded through the proximal end of cylinder 4 and moved distally through the interior thereof until the end cap 38 of cartridge 8 is contacted by and located below the first set of radially projecting catches 32 at the flexible arms 30 of needle carrying hub 6. More particularly, the cartridge 8 causes a slight rotation of the arms 30 of hub 6, such that the end cap 38 of the cartridge is retained by a snap-fit engagement between catches 32 and 34. Accordingly, the cartridge 8 and the proximally projecting end of needle 28 are maintained in spaced, coaxial alignment with one another, so as to avoid a possible corrosion or oxidation of the needle, as might otherwise be caused by contact between the needle and the fluid medication within cartridge 8. Moreover, separation of the needle 28 and cartridge 8 is also desirable during packaging, because certain medications may be rendered inert when exposed to air.

Once the assembly of FIG. 2 is completed, the syringe 1 is packaged and sterilized. The sterilized package is then ready for distribution and use by appropriate medical workers.

Figure 3:
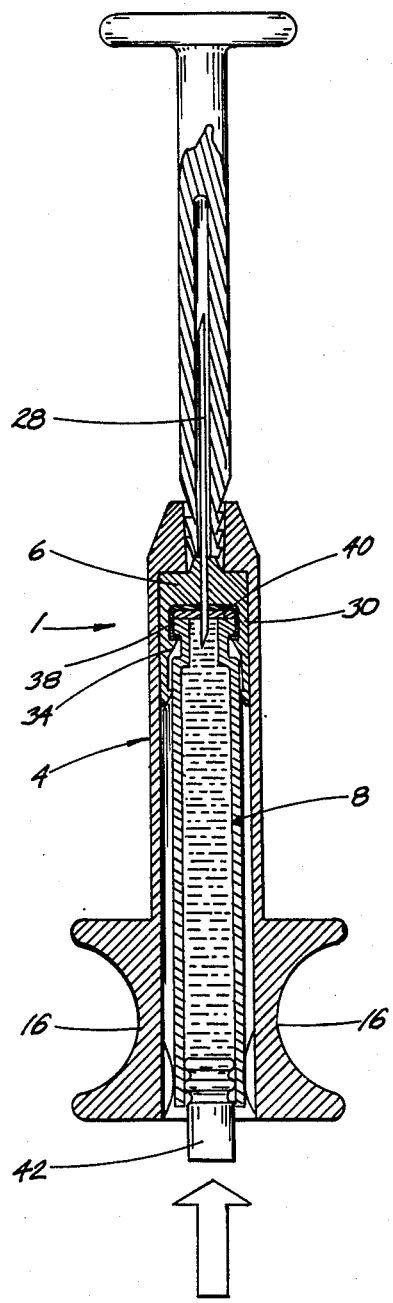
FIGS. 3-5 detail the operation of the syringe for administering an injection from a pre-filled medication cartridge to a targeted tissue area.

Operation of the syringe 1 is now described while referring to FIGS. 3-6 of the drawings. In FIG. 3, the sterilized syringe 1 is removed from its package (not shown), whereupon the user places his thumb behind the rubber piston 42 of medication cartridge 8 and his index and middle fingers ahead of (or within) the opposing finger ledges 16. The user depresses the piston 42 (in the direction indicated by the reference arrow) so as to correspondingly force the cartridge 8 to move distally within syringe cylinder 4. Accordingly, the end cap 38 of cartridge 8 is moved into contact with and below the second set of catches 34 which projects from arms 30 of needle carrying hub 6. This additional distal movement of cartridge 8 within cylinder 4 also causes the rubber diaphragm 40 of cartridge 8 to be impaled by the proximally projecting end of needle 28, such that needle 28 communicates with the fluid contents of the cartridge.

Figure 4:
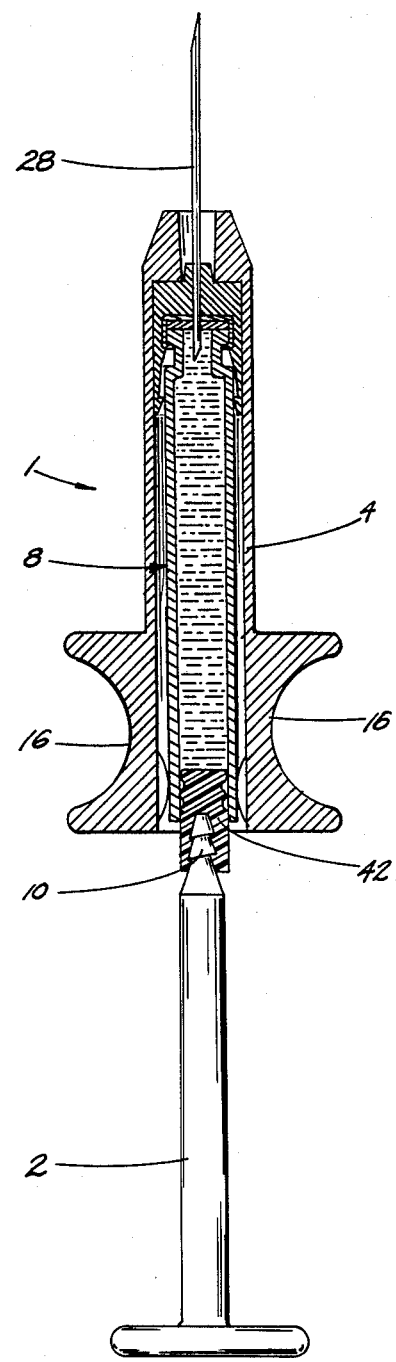

In FIG. 4, needle sheath 2 is removed from the needle 28 by detaching (e.g. pulling) the threaded end 10 of sheath 2 out of engagement with the distal bore of the syringe cylinder 4. Hence, the distally projecting end of needle 28 is exposed in order to inject fluid from cartridge 8 to a targeted tissue area. The needle sheath 2 is then attached to the rubber piston 42 of cartridge 8 to thereby form a piston assembly comprising an elongated piston stem (i.e. needle sheath 2) and a plunger head (e.g. piston 42). More particularly, the threaded end 10 of needle sheath 2 is provided with a configuration which is commonly referred to as a Morse Taper. The threaded end 10 of needle sheath 2 is inserted within and rotated or screwed slightly into the complementary receptacle (designated 44 in FIG. 2) formed in the piston 42. However, it may be necessary for the user to first insert his fingers within the opposing finger ledges 16 to thereby squeeze the cartridge 8 and prevent a rotation thereof when rotating the tapered end 10 into receptacle 44. Nevertheless, by virtue of the Morse taper, the needle sheath (hereinafter referred to as the piston stem 2-1) and piston 42 are easily and reliably connected together to form the aforementioned piston assembly.

Figure 5:
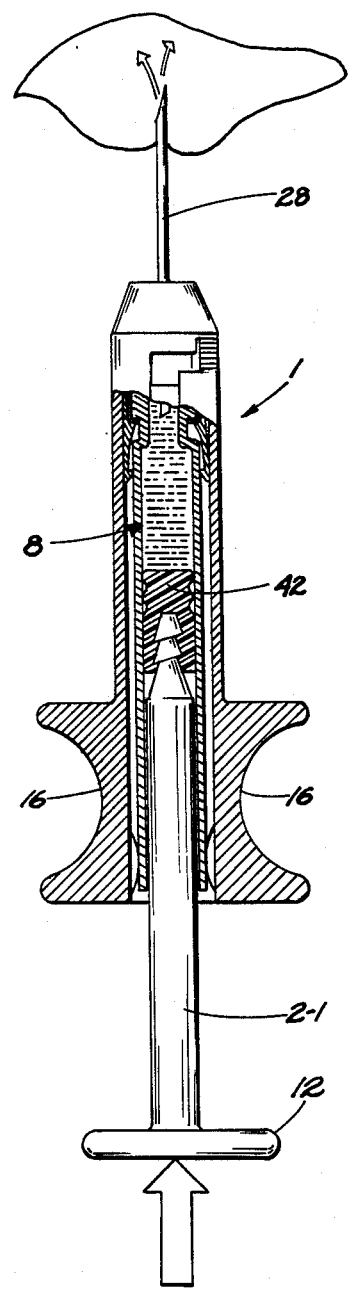

In FIG. 5, the syringe 1 is shown with the needle 28 being located at a targeted tissue area so that fluid medication can be injected thereto from cartridge 8. More particularly, the user places his index and middle fingers within the opposing finger ledges 16. The user's thumb is placed against the flange 12 of piston stem 2-1, and a distally directed force is exerted upon flange 12 to drive the piston assembly through the interior of cartridge 8, whereby medication is expulsed from cartridge 8 via needle 28.

Figure 6:
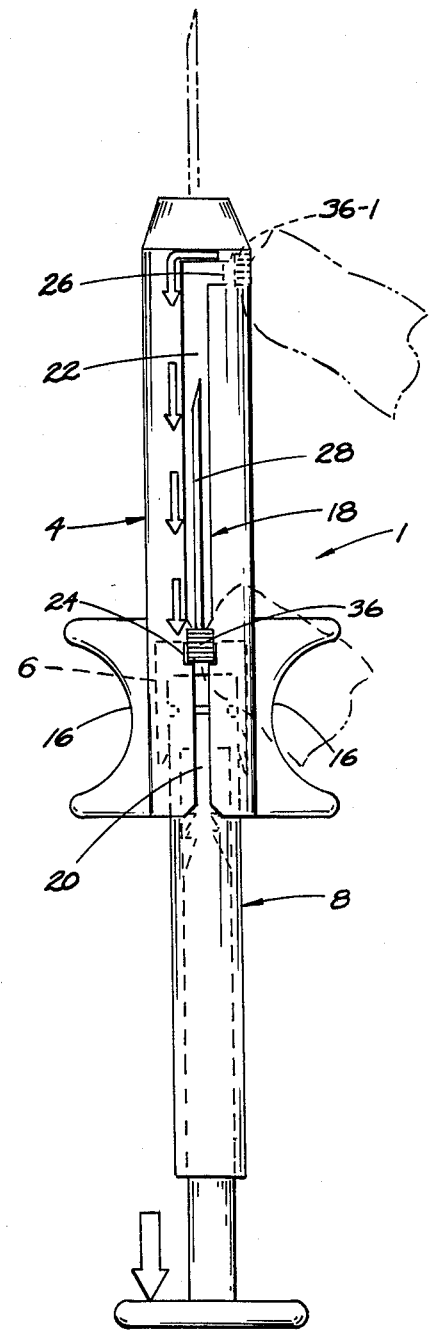
FIG. 6 illustrates the steps for relocating the needle cannula from a position projecting outwardly and distally from the syringe cylinder to a position retracted and locked within the cylinder to permit the syringe to be safely handled and discarded after use.

After completion of the injection process, and now referring to FIG. 6, the needle is withdrawn from the targeted tissue area. According to an important advantage of the present invention, the needle may be retracted and locked within the syringe cylinder 4 to permit a safe disposal of the syringe 1, while avoiding an accidental needle strike and the possible spread of a contagious disease. More particularly, and with the user's index and middle fingers remaining in place in finger ledges 16, the user places the index finger (shown in phantom) of his opposite hand in contact with the needle position control button (shown in phantom and designated 36-1) at the locked position within needle extension detent 26. The control button 36 is moved (i.e. rotated) out of the locked position of detent 26 and into the distal guide portion 22 of the axial slot 18. The user then slides the control button 36 in a proximal direction through axial slot 18 until control button 36 is received within the needle retraction detent 24. Inasmuch as the needle position control button 36 is connected to the needle carrying hub 6, a proximal movement of the control button 36 (along a path indicated by the reference arrows) causes a corresponding proximal relocation of both the needle carrying hub 6 and the now empty medication cartridge 8, as well as a retraction of the needle 28 completely within the syringe cylinder 4.

The resilient nature of the cylinder 4 permits needle position control button 36 to ride through the distal guide portion 22 and adjacent taper of axial slot 18. That is, the control button 36 is of a sufficient size to cause a stress in and slight rotation of the opposing walls of cylinder 4 which define slot 18. Once the control button 36 is received within the needle retraction detent 24, the cylinder walls will automatically rotate back to their pre-stressed condition. However, the needle position control button 36 will be permanently locked within detent 24 with the needle 28 completely shielded by the syringe cylinder 4. Thus, the syringe 1 may be safely handled and discarded after use. Moreover, an empty syringe is rendered safe against accidental needle strikes and the spread of a possibly contagious disease by eliminating the need for health care workers to either handle or cut the needle prior to disposal, as has heretofore been required with conventional syringes.

It will be apparent that while a preferred embodiment of the invention has been shown and described, various modifications and changes may be made without departing from the true spirit and scope of the invention. For example, the syringe 1 of the present invention has particular utility in a dental office for administering a local anesthetic to the mouth of a patient undergoing treatment. However, it is to be understood that the present syringe is also ideally suited for other applications which require a pre-filled medication cartridge. What is more, because of the dual role played by the needle sheath (i.e. as a protective sheath and a piston stem), the number of parts, size, and the cost of the syringe may be reduced.

Having thus set forth a preferred embodiment of the invention, what is claimed is:

1. A syringe comprising a cylinder having distal and proximal ends and a cartridge containing a supply of medication and being located within said cylinder, said syringe further comprising:
   a double ended hypodermic needle;
   means for carrying said needle located within said cylinder such that a first end of said needle projects outwardly and distally from said cylinder for administering an injection of the medication supply and the opposite end of said needle extends proximally and inwardly into said cylinder for fluid communication with the medication supply of said cartridge, said needle carrying means having a position control button connected thereto; and
   axial guide slot means formed in said cylinder between the distal and proximal ends thereof, the button of said needle carrying means being receivable in and movable through said guide slot means for controlling the location of said needle carrying means and the needle carried thereby relative to the interior of said cylinder.

2. The syringe recited in claim 1, wherein said carrying means includes a plurality of arms for engaging and retaining said cartridge in communication with the proximally extending end of said hypodermic needle.

3. The syringe recited in claim 1, wherein said axial guide slot means has first and second locking detents which are spaced from one another, the button of said needle carrying means being locatable at said first locking detent such that said first needle end projects outwardly and distally from said cylinder, said button being removable from said first locking detent and movable through said guide slot means to said second locking detent to relocate said needle carrying means proximally through said cylinder and thereby retract said needle completely therewithin.

4. The syringe recited in claim 1, further comprising a movable piston located at one end of said medication cartridge; and covering means for sheathing and protecting the first, distally projecting end of said needle, said covering means being removable from said first needle end and connectable to the piston of said cartridge at the proximal end of said cylinder for forming a piston stem to drive said piston through said cartridge to expulse medication therefrom.

5. The syringe recited in claim 4, wherein said covering means is an elongated, hollow needle sheath.

6. The syringe recited in claim 4, wherein one end of said covering means is provided with a terminal to be received within and detachably connected to said cylinder at the distal end thereof.

7. The syringe recited in claim 6, wherein the terminal of said covering means has a tapered thread.

8. The syringe recited in claim 7, wherein the piston of said cartridge is provided with a receptacle to receive therewithin the tapered thread of said covering means for connecting said covering means to said piston and thereby forming said piston stem for driving said piston through said cartridge.

9. The syringe recited in claim 3, wherein said axial guide slot means includes an area having a relatively wide width communicating with said first locking detent and an area having a relatively narrow width communicating with said second locking detent.

10. The syringe recited in claim 3, wherein said first locking detent is transversely aligned with respect to said axial guide slot means.

11. A syringe including a cylinder having distal and proximal ends, said syringe comprising:

a medication filled cartridge located within said cylinder and having a movable piston at one end thereof;

a double ended needle;

means for carrying said needle located within said cylinder such that a first end of said needle projects outwardly and distally from said cylinder for administering an injection and the opposite end of said needle extends proximally and inwardly into said cylinder for communication with said cartridge, said needle carrying means having a position control button connected thereto;

axial guide slot means formed in said cylinder between the distal and proximal ends thereof, the button of said needle carrying means being receivable in and movable through said guide slot means for controlling the location of said needle carrying means and the needle carried thereby relative to the interior of said cylinder; and covering means for sheathing and protecting the distally projecting end of said needle, said covering means being removable from said needle and connectable to the piston of said cartridge at the proximal end of said cylinder for forming a piston stem to drive said piston through said cartridge to expulse medication therefrom.

12. A syringe having a cylinder having distal and proximal ends and a cartridge containing a supply of medication, said syringe further comprising:

a double ended hypodermic needle, a first end of said needle projecting inwardly into said cylinder to penetrate said cartridge and communicate with the medication supply thereof;

means for carrying said needle located within and movable axially through said cylinder between relatively distal and proximal positions, such that the opposite end of said needle projects outwardly from said cylinder for administering an injection when said needle carrying means is located at said distal position within said cylinder;

position control means extending from said needle carrying means and movable therewith; and axial guide slot means formed in said cylinder between the proximal and distal ends thereof, said position control means being received in and movable axially through said guide slot means for relocating said needle carrying means from said distal position within said cylinder to said proximal position, so as to retract said needle into said cylinder.

13. The syringe recited in claim 12, wherein said needle carrying means includes a plurality of arms extending axially therefrom, said arms having means for engaging and retaining said medication cartridge in communication with the first end of said needle.

14. The syringe recited in claim 12, wherein said axial guide slot means has first and second locking detents which are spaced from one another, said position control means being located at said first locking detent such that said needle carrying means is located at said distal position within said cylinder and said needle projects outwardly from said cylinder for administering an injection, or said position control means being located at said second locking detent such that said needle carrying means is located at said proximal position within said cylinder and said needle is retracted into said cylinder.

15. The syringe recited in claim 14, when said axial guide slot means includes an area having a relatively wide width communicating with said first locking detent and an area having a relatively narrow width communicating with said second locking detent.

16. The syringe recited in claim 14, wherein said first locking detent is transversely aligned with respect to said axial guide slot means.

* * * * *